(12) United States Patent
Bernick et al.

(10) Patent No.: US 10,059,984 B2
(45) Date of Patent: Aug. 28, 2018

(54) SALT-TOLERANT DNA POLYMERASES

(75) Inventors: David Bernick, Santa Cruz, CA (US);
Andrew Holmes, Santa Cruz, CA (US);
Jeffrey Nivala, Santa Cruz, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/126,421

(22) PCT Filed: Jun. 10, 2012

(86) PCT No.: PCT/US2012/041802
§ 371 (c)(1),
(2), (4) Date: Dec. 14, 2013

(87) PCT Pub. No.: WO2012/173905
PCT Pub. Date: Dec. 20, 2012

(65) Prior Publication Data
US 2014/0113291 A1    Apr. 24, 2014

Related U.S. Application Data

(60) Provisional application No. 61/497,524, filed on Jun. 16, 2011.

(51) Int. Cl.
*C12Q 1/68*    (2018.01)
*C12Q 1/686*   (2018.01)
*C12N 9/12*    (2006.01)
*C12Q 1/6844*  (2018.01)
*C12Q 1/6869*  (2018.01)

(52) U.S. Cl.
CPC ............ *C12Q 1/686* (2013.01); *C12N 9/1252* (2013.01); *C12Q 1/6844* (2013.01); *C12Q 1/6869* (2013.01)

(58) Field of Classification Search
None
See application file for complete search history.

(56) References Cited

U.S. PATENT DOCUMENTS

| 2,198,222 | A | 4/1940 | Musher |
| 5,691,142 | A | 11/1997 | Dahlberg et al. |
| 5,968,743 | A | 10/1999 | Matsunaga et al. |
| 6,333,159 | B1 | 12/2001 | Barnes et al. |
| 2007/0264660 | A1 * | 11/2007 | Matsui et al. ............... 435/6 |

FOREIGN PATENT DOCUMENTS

WO    WO-01/14568 A1 *    3/2001

* cited by examiner

*Primary Examiner* — Carla J Myers
(74) *Attorney, Agent, or Firm* — Kilpatrick Townsend & Stockton LLP

(57) ABSTRACT

Four novel sequences of type B DNA polymerases and variants and analogues thereof useful for applications involving DNA polymerization in high salt conditions.

7 Claims, 1 Drawing Sheet

Specification includes a Sequence Listing.

SALT-TOLERANT DNA POLYMERASES

RELATION TO OTHER APPLICATIONS

This U.S. National Phase application under 35 U.S.C. 371 claims the benefit of PCT application No. PCT/US12/41802 filed 10 Jun. 2012, which itself claims the benefit of U.S. Provisional Application No. 61/497,524 filed 16 Jun. 2011 and titled Salt-tolerant DNA polymerases.

GOVERNMENT SPONSORSHIP

This invention was made with support from a UCSC/SOE start-up grant No. 19900-4041. The government has certain rights in the invention.

FIELD OF THE INVENTION

DNA polymerases that function at high salt concentrations.

BACKGROUND

DNA polymerase enzymes are naturally-occurring intracellular enzymes, and are used by a cell to replicate a nucleic acid strand using a template molecule to manufacture a complementary nucleic acid strand. The in-vitro use of enzymes having DNA polymerase activity has in recent years become more common in a variety of biochemical applications including cDNA synthesis and DNA sequencing reactions (see Sambrook et al., (2nd ed. Cold Spring Harbor Laboratory Press, 1989) hereby incorporated by reference herein), and amplification of nucleic acids by methods such as the polymerase chain reaction (PCR) (Mullis et al., U.S. Pat. Nos. 4,683,195, 4,683,202, and 4,800,159, hereby incorporated by reference herein) and RNA transcription-mediated amplification methods (e.g., Kacian et al., PCT Publication No. WO91/01384 which enjoys common ownership with the present application and is hereby incorporated by reference herein). Methods such as PCR make use of cycles of primer extension through the use of a DNA polymerase activity, followed by thermal denaturation of the resulting double-stranded nucleic acid in order to provide a new template for another round of primer annealing and extension.

Various scientific and industrial applications exist in which it would be advantageous to use a DNA polymerase that function efficiently at high salt concentrations. In sequencing, GC compressions can be resolved by using high salt concentrations. In nanopore sequencing high salt concentration boosts the signal to noise ratio for ionic-current-based nanopore measurements. Salt tolerant DNA polymerases may be found among members of the extreme halophiles, in which salt tolerance is achieved not by exclusion of monovalent ions from the cytosol, but by adapting intracellular machinery function in elevated salt. As an example of salt tolerance among members of the extreme halophiles, malate dehydrogenase from the archaeal halophile Haloarcula marismortui incorporates a salt-adaptive strategy where the high ionic concentration from the environment is not only tolerated but is incorporated within the protein. Sodium and chloride ions are found incorporated within the molecule itself. When considering viruses that infect extreme halophiles, not only are proteins of the viral capsid exposed directly to the environment, but the proteins of the replication machinery must operate effectively within the elevated salt environment of its archaeal host.

Phi29 is a widely used and commercially successful salt tolerant DNA polymerase from *bacillus* phage Phi29, however its salt tolerance is limited, and in 1 M KCl there is no detectable binding of the enzyme to the DNA substrate.

It would be desirable to identify DNA polymerases that can function at elevated salt concentrations, for example at concentrations of at least 5%, 10%, 20% or 30% wt/vol salt, such as KCl or NaCl.

SHORT DESCRIPTION OF THE INVENTION

The invention encompasses isolated DNA polymerase comprising an amino acid sequence having at least 60% sequence identity to an amino acid sequence selected from the group consisting of SEQ ID Nos 2, 4, 6 and 8. Percent sequence identity between the claimed DNA polymerase of the invention and SEQ ID Nos 2, 4, 6 and 8 may, in various embodiments, be, for example, at least 60%, or 70% or 80% or 90% or 95% or 99% or 100% identity.

The DNA polymerases of the invention catalyze DNA polymerization under ionic conditions of at least 5% and up to 25% KCl (or other monovalent salt) wt/vol, wherein the rate (or average rate) of polymerization is at least 20 bases per minute. Salt concentrations may also be expressed as molarities, and The DNA polymerases of the invention catalyze DNA polymerization in monovalent salt concentrations in excess of 0.75M up to 4M.

The invention encompasses a biologically active fragment of RD0, RD1, RD2, or RD3, that catalyzes DNA polymerization, where the fragment comprises a polypeptide of at least 20 contiguous amino acid residues of an amino acid sequence selected from the group consisting of SEQ ID Nos 2, 4, 6 and 8.

The invention encompasses an isolated polynucleotide, the polynucleotide having at least 60% sequence identity to a polynucleotide sequence selected from the group consisting of SEQ ID Nos 1, 3, 5 and 7. Percent sequence identity of the claimed polynucleotides may be at least 50%, in various embodiments, be for example, at least 60%, or 70% or 80% or 90% or 95% or 99% or 100% identity. The isolated polynucleotide may have a sequence selected from the group consisting of SEQ ID Nos 2, 4, 6 and 8.

The invention further encompasses polynucleotides described cloned into vectors and host cells comprising such vectors. The claimed polynucleotides may be recombinant and/or synthetic.

The invention includes or variants and analogues of any of the foregoing.

The invention further encompasses a method for DNA synthesis at high salt concentration, comprising: a) providing a DNA polymerase comprising an amino acid sequence having at least 60% sequence identity to an amino acid sequence selected from the group consisting of SEQ ID Nos 2, 4, 6 and 8, b) contacting a DNA polymerase with a nucleic acid template under conditions of high salt concentration, wherein high salt concentration is defined as ionic conditions of at least 3% salt KCl (or other monovalent salt) wt/vol, c) effecting template dependent synthesis of DNA. In such methods the high salt concentration may comprise conditions of between 5% and 25% salt KCl (or other monovalent salt) wt/vol.

The invention further encompasses a method for detecting a target polynucleotide in a sample, said method comprising the steps of a) providing a labelled polynucleotide probe having a sequence that comprises at least 16 contiguous nucleotides of the polynucleotide sequence of RD0, RD1, RD2, or RD3, and b) contacting said probe with a sample putatively containing a target polynucleotide complementary to the probe, c) hybridizing the probe and the target polynucleotide, d) detecting the presence or absence of said hybridization complex.

Additionally, the invention further encompasses kit comprising a sequencing reagent for DNA sequencing or amplification, the reagent comprising a high salt tolerant DNA polymerase having at least 60% sequence identity to a polypeptide sequence selected from the group consisting of RD0, RD1, RD2, and RD3.

DESCRIPTION OF THE SEQUENCE LISTING

The application discloses sequences in standard FASTA format, for both nucleotide and protein, for RD0, RD1, RD2, and RD3 (SEQ IDs 1 to 8). Also disclosed are the sequence for the closest currently known sequences from the salterproviruses His1 and His2 (SEQ IDs 9 to 12). The information recorded in electronic form (if any) submitted (under Rule 13 ter if appropriate) with this application is identical to the sequence listing as contained in the application as filed. The sequences represented in the accompanying sequence listing are as follows:

SEQ ID No. 1. >rd0-nuc=the nucleotide sequence for rd0
SEQ ID No. 2. >rd0=the amino acid sequence for rd0
SEQ ID No. 3. >rd1-nuc=the nucleotide sequence for rd1
SEQ ID No. 4. >rd1=the amino acid sequence for rd1
SEQ ID No. 5. >rd2-nuc=the nucleotide sequence for rd2
SEQ ID No. 6. >rd2=the amino acid sequence for rd2
SEQ ID No. 7. >rd3-nuc=the nucleotide sequence for rd3
SEQ ID No. 8. >rd3=the amino acid sequence for rd3
SEQ ID No. 9. >His1V_gp12=the nucleotide sequence for His1V_gp12
SEQ ID No. 10. >His1V_gp12 length=717=the amino acid sequence for His1V_gp12
SEQ ID No. 11. >His2V_gp14=the nucleotide sequence for His2V_gp14
SEQ ID No. 12. >His2V_gp14 length=720=the amino acid sequence for His2V_gp14

The salterproviruses His1 and His2 sequences are viral sequences, and as such, they will not have a genus-species. These were not discovered by our work and are provided as reference sequences. Michael Dyall-Smith and coworkers. The other 8 sequences are derived from metagenomic sequences found by sequencing DNA isolated from a pond at location A23. We suspect that these are vial sequences but we cannot know what organism or virus they are from.

DESCRIPTION OF THE FIGURES

FIG. 1. shows a Sequence comparison between Phi29 (SEQ ID NO:13), his1_gp12 (SEQ ID NO:10), his1_gp14 (SEQ ID NO:12)and rd0 (SEQ ID NO:2), rd1 (SEQ ID NO:4), rd2 (SEQ ID NO:6) and rd3 (SEQ ID NO:8). In the key from top to bottom, the word Exonuclease is the first arrow. Palm is the second arrow. TRP1 is the third arrow. Fingers is the forth arrow. TRP2 is the fifth arrow. And Thumb is the last arrow.

GENERAL REPRESENTATIONS CONCERNING THE DISCLOSURE

The embodiments disclosed in this specification are exemplary and do not limit the invention. Other embodiments can be utilized and changes can be made. As used in this specification, the singular forms "a", "an", and "the" include plural reference unless the context clearly dictates otherwise. Thus, for example, a reference to "a part" includes a plurality of such parts, and so forth. The term "comprises" and grammatical equivalents thereof are used in this specification to mean that, in addition to the features specifically identified, other features are optionally present. Where reference is made in this specification to a method comprising two or more defined steps, the defined steps can be carried out in any order or simultaneously (except where the context excludes that possibility), and the method can optionally include one or more other steps which are carried out before any of the defined steps, between two of the defined steps, or after all the defined steps (except where the context excludes that possibility). Where reference is made herein to "first" and "second" features, this is generally done for identification purposes; unless the context requires otherwise, the first and second features can be the same or different, and reference to a first feature does not mean that a second feature is necessarily present (though it may be present). Where reference is made herein to "a" or "an" feature, this includes the possibility that there are two or more such features.

This specification incorporates by reference all documents referred to herein and all documents filed concurrently with this specification or filed previously in connection with this application, including but not limited to such documents which are open to public inspection with this specification.

Where KCl is mentioned, this salt is used as an example only, and 'KCl' may be substituted in all instances for any other salt such as any monovalent salt.

The information recorded in electronic form (if any) submitted (under Rule 13ter if appropriate) with this application is identical to the sequence listing as contained in the application as filed.

Definitions

The term "amino acid sequence" refers to an oligopeptide, peptide, polypeptide, or protein sequence, or a fragment of any of these.

The term "amplification" relates to the production of additional copies of a nucleic acid sequence e.g., using polymerase chain reaction (PCR).

The term "antibody" refers to intact immunoglobulin molecules as well as to fragments thereof, such as Fab, F(ab')2, and Fv fragments, which are capable of binding an epitopic determinant.

The term "similarity" refers to a degree of complementarily. There may be partial similarity or complete similarity. The word "identity" may substitute for the word "similarity." A partially complementary sequence that at least partially inhibits an identical sequence from hybridizing to a target nucleic acid is referred to as "substantially similar."

The phrase "percent identity" as applied to polynucleotide or polypeptide sequences refers to the percentage of residue matches between at least two sequences aligned using a standardized algorithm such as any of the BLAST suite of programs (e.g., blast, blastp, blastx, nucleotide blast and protein blast) using, for example, default parameters. BLAST tools are very commonly used and are available on the NCBI web site.

A "variant" of a particular polypeptide sequence is defined in this disclosure as a polypeptide sequence having at least 40% sequence identity to the particular polypeptide sequence over a certain length of one of the polypeptide sequences using blastp with the "BLAST 2 Sequences" tool set at default parameters. Such a pair of polypeptides may show, for example, at least 50%, at least 60%, at least 70%, at least 80%, at least 86%, at least 90%, at least 95%, or at least 98% or greater sequence identity over a certain defined length of one of the polypeptides.

The word "homologue" when used to describe a sequence refers to a sequence that is a variant of another and wherein the two sequences are evolutionarily related. In the present disclosure, when a particular gene or protein is referred to, the term is meant to encompass homologues and orthologues, variants, derivatives, and mutants of such a gene or protein. The present invention is not limited to embodiments employing the exact sequence of any of the disclosed proteins, polypeptides, polynucleotides etc, but encompasses any variant that is related by structure, sequence, function or is derived in any way from the named protein. For example, the present invention encompasses polypeptides having, for example, at least 30% primary amino acid sequence similarity to a an envelope glycoprotein over a length of at least 100 amino acid residues, or in other embodiments, at least 40%, 50%, 75%, 90% or 99% primary protein sequence similarity.

"Variants and analogues" of polynucleotides encompass polynucleotides that show structural similarity to the polynucleotide of which it is an analogue or variant. Structural similarity for polynucleotides refers to sequence similarity. A polynucleotide analogue may have, for example, at least 99%, 95%, 90%, 85%, 80%, 70%, 60%, 50%, or at least 40% similarity over the entire length of the original polynucleotide. Often variants that share functional motifs have a good deal less than 40% overall sequence similarity, and yet may still be reasonably described as variants or analogues. Alternatively it may have a similarity of at least 99%, 95%, 90%, 85%, 80%, 70%, 60%, 50%, or at least 40%, 30% or at least 20% similarity over a shorter length, for example over at least 1000 nucleotides, or at least 500, at least 250, at least 150, at least 100, at least 50 or at least 25 polynucleotides. Variants may be derivatives of the polynucleotide of which they are a variant, they may be chemically or biochemically modified and have one or more amino nucleotide substitutions, additions, and/or deletions. Variants may share certain functionally significant motifs with the polynucleotide of which they are a variant. These motifs may encode the portion of a protein that includes the active site of a protein, the portion that is essential to enzymatic activity. Sequence similarities and homologies may be reliably and consistently determined by using any of the well known Basic Local Alignment Search Tool (BLAST) software tools.

Percent identity between polynucleotide sequences may be determined using the default parameters of the CLSUATL W algorithm as incorporated into the MEGA-LIGN version 3.12e sequence alignment program. For pairwise alignments of polynucleotide sequences, the default parameters are set as follows: Ktuple=2, gap penalty=5, window=4, and "diagonals saved"=4. The "weighted" residue weight table is selected as the default. Percent identity is reported by CLSUATL W as the "percent similarity" between aligned polynucleotide sequence pairs.

Alternatively, a suite of commonly used and freely available sequence comparison algorithms is provided by the National Center for Biotechnology Information (NCBI) Basic Local Alignment Search Tool (BLAST) (Altschul, S. F. et al. (1990) J. Mol. Biol. 215:403-410). The "BLAST 2 Sequences" tool can be used for both blastn and blastp (discussed below). BLAST programs are commonly used with gap and other parameters set to default settings. For example, to compare two nucleotide sequences, one may use blastn with the "BLAST 2 Sequences" tool Version 2.0.9 (May 7, 1999) set at default parameters. Such default parameters may be, for example:

Matrix: BLOSUM62
Reward for match: 1
Penalty for mismatch: −2
Open Gap: 5 and Extension Gap: 2 penalties
Gap×drop-off: 50
Expect: 10
Word Size: 11
Filter: on Percent identity may be measured over the length of an entire defined sequence, for example, as defined by a particular SEQ ID number, or may be measured over a shorter length, for example, over the length of a fragment taken from a larger, defined sequence, for instance, a fragment of at least 20, at least 30, at least 40, at least 50, at least 70, at least 100, or at least 200 contiguous nucleotides. Such lengths are exemplary only, and it is understood that any fragment length supported by the sequences shown herein, in the tables, figures, or Sequence Listing, may be used to describe a length over which percentage identity may be measured.

Percent identity between polypeptide sequences may be determined using the default parameters of the CLSUATL W algorithm as incorporated into the MEGALIGN version 3.12e sequence alignment program (described and referenced above). For pairwise alignments of polypeptide sequences using CLSUATL W, the default parameters are set as follows: Ktuple=1, gap penalty=3, window=5, and "diagonals saved"=5. The PAM250 matrix is selected as the default residue weight table. As with polynucleotide alignments, the percent identity is reported by CLSUATL W as the "percent similarity" between aligned polypeptide sequence pairs.

Alternatively the NCBI BLAST software suite may be used. For example, for a pairwise comparison of two polypeptide sequences, one may use the "BLAST 2 Sequences" tool Version 2.0.9 (May 7, 1999) with blastp set at default parameters. Such default parameters may be, for example:

Matrix: BLOSUM62
Open Gap: 11 and Extension Gap: 1 penalties
Gap×drop-off: 50
Expect: 10
Word Size: 3
Filter: on Percent identity may be measured over the length of an entire defined polypeptide sequence, for example, as defined by a particular SEQ ID number, or may be measured over a shorter length, for example, over the length of a fragment taken from a larger, defined polypeptide sequence, for instance, a fragment of at least 15, at least 20, at least 30, at least 40, at least 50, at least 70 or at least 150 contiguous residues. Such lengths are exemplary only, and it is understood that any fragment length supported by the sequences shown herein, in the tables, figures or Sequence Listing, may be used to describe a length over which percentage identity may be measured.

Detailed Description of the Invention

Described here are four novel sequences of type B DNA polymerases and variants and analogues thereof that can be used in applications involving DNA in high salt conditions. These DNA polymerases are stable and operate under ionic conditions of at least 5% salt (KCl or other monovalent salt) wt/vol, and up to 25% wt/vol. These molecules remain stable at salt concentrations well beyond any currently commercially available DNA polymerase and provide polymerization at a rate (or an average rate) of at least 20 bases per minute.

The four novel Halophilic DNA polymerases, called RD0, RD1, RD2, and RD3, are described and their polynucleotide and protein sequences are disclosed. The polymerases were isolated from a metagenome of viruses of halophilic archebacteria.

The high salt tolerance of these DNA polymerases may be very useful for various applications in which high salt concentration is an advantage. For example, the polymerases are useful for sequencing in which they provide better resolution of GC rich compressions. Additionally the polymerases are useful for nanopore sequencing where a high salt concentration will boost the signal to noise ratio for ionic-current-based nanopore measurements.

The closest homologue to RD0, RD1, RD2, and RD3 appears to be a protein derived the known halophilic salterproviruses viruses His1 (His1V_gp12 YP_529524.1) and His2 (His2V_gp14 YP_529644.1) which demonstrates a 38%-50% identity to RD0, RD1, RD2, and RD3. The functions of these His1 and His2 proteins is unknown, although it may be speculated that they may have DNA polymerase activity.

| Percent ID* | | |
| --- | --- | --- |
| | His1 | His2 |
| RD0 | 38% | 40% |
| RD1 | 40% | 50% |
| RD2 | 44% | 43% |
| RD3 | 38% | 39% |

*Identities to His1/His2 DNA polymerases (Blastp, wordsize 2, Blosum45)

RD0, RD1, RD2, and RD3 all possess the TPR2 motif, a functional motif found TPR2, a specific subdomain of protein-priming DNA polymerases.

The commercially available Phi29 DNA polymerase is 18.1%, 18.4%, 20.4% and 19.3% identical at the protein level with RD0, RD1, RD2, and RD3 respectively. Phi29 is a widely used and commercially successful salt tolerant DNA polymerase from *bacillus* phage Phi29, however its salt tolerance is limited and in 1 M KCl there is no detectable binding of the enzyme to the DNA substrate.

The DNA polymerases of the invention are stable and exhibit appreciable enzymatic activity under ionic conditions of at least 3% salt (KCl or other monovalent salt) wt/vol, or in other embodiments, at least 5% wt/vol Monovalent salt, or at least 7% wt/vol Monovalent salt, or at least 10% wt/vol Monovalent salt, or at least 15% wt/vol Monovalent salt, or at least 20% wt/vol Monovalent salt, or at least 25% wt/vol Monovalent salt. The salt may be others salts other than KCl, such as NaCl; KCl is given only as an example. The important property is that the DNA polymerases of the invention function under high salt concentrations.

Embodiments

In one aspect, the invention provides isolated DNA polymerases comprising:

a) an amino acid sequence selected from SEQ ID Nos 2, 4, 6 and 8, b) an amino acid sequence having at least 60% (or in other embodiments at least 50%, at least 70%, at least 80%, at least 90% and at least 95%) sequence identity to an amino acid sequence selected from the group consisting of SEQ ID Nos 2, 4, 6 and 8, c) a biologically active fragment of RD0, RD1, RD2, or RD3, where the fragment comprises a polypeptide of at least 20 contiguous amino acid residues of an amino acid sequence selected from the group consisting of SEQ ID Nos 2, 4, 6 and 8, or d) an immunogenic fragment of RD0, RD1, RD2, or RD3, where the fragment comprises a polypeptide of at least 10 (or 15, 20, 25, 30, 35, 40, 50 or 60) contiguous amino acid residues of an amino acid sequence selected from the group consisting of SEQ ID Nos 2, 4, 6 and 8, or variants and analogues of any of the foregoing.

The invention further encompasses an isolated polynucleotide encoding any of the above polypeptides or amino acid sequences and or variants and analogues thereof, including polynucleotides with sequences selected from SEQ ID Nos 1, 3, 5 and 7, and polynucleotides having at least 60% (or in other embodiments at least 70%, at least 80%, at least 90% and at least 95%) sequence identity to an polynucleotide sequence selected from the group consisting of SEQ ID Nos 1, 3, 5 and 7.

Additionally, the invention provides a recombinant and/or synthetic polynucleotide comprising a promoter sequence operably linked to a polynucleotide encoding any of the above polypeptides or amino acid sequences, or to a polynucleotide disclosed herein such as polynucleotides with sequences selected from SEQ ID Nos 1, 3, 5 and 7. The invention also includes recombinant polynucleotide comprising a promoter sequence operably linked to a polynucleotide having at least 60% (or in other embodiments at least 70%, at least 80%, at least 90% and at least 95%) sequence identity to an polynucleotide sequence selected from the group consisting of SEQ ID Nos 1, 3, 5 and 7.

The invention also provides a method for producing any of the above polypeptides or amino acid sequences. The method comprises a) culturing a cell under conditions suitable for expression of the polypeptide, wherein said cell is transformed with a recombinant polynucleotide comprising a promoter sequence operably linked to a polynucleotide encoding the polypeptide, and b) recovering the polypeptide so expressed.

Additionally, the invention provides a method for detecting a target polynucleotide in a sample, said target polynucleotide comprising (1) the polynucleotide sequence of RD0, RD1, RD2, or RD3, (2) a polynucleotide sequence that comprises at least 8 or at least 12 or at least 16 or at least 18 or at least 20 or at least 24 or at least 30 or at least 40 contiguous nucleotides of the polynucleotide sequence of RD0, RD1, RD2, or RD3, (3) a polynucleotide sequence that encodes a high salt tolerant DNA polynucleotide having at least 60% sequence identity to a polynucleotide sequence selected from the group consisting of the polynucleotide sequence of RD0, RD1, RD2, and RD3, (4) a polynucleotide sequence complementary to any of the foregoing. The method comprises a) hybridizing the sample with a probe comprising at least 16 contiguous nucleotides comprising a sequence complementary to said target polynucleotide in the sample, and which probe specifically hybridizes to said target polynucleotide, under conditions whereby a hybridization complex is formed between said probe and said target polynucleotide, and b) detecting the presence or absence of said hybridization complex, and optionally, if present, the amount thereof. In one alternative, the probe comprises at least 30 contiguous nucleotides. In another alternative, the probe comprises at least 60 contiguous nucleotides.

The invention further provides sequencing reagents for DNA sequencing or amplification, the reagent(s) comprising a high salt tolerant DNA polymerase with an amino acid sequence of RD0, RD1, RD2, or RD3, or a high salt tolerant DNA polynucleotide having at least 60% sequence identity (or in other embodiments at least 70%, at least 80%, at least 90% and at least 95%) to a polypeptide sequence selected from the group consisting of RD0, RD1, RD2, and RD3.

The invention also encompasses an isolated polynucleotide, the polynucleotide having at least 60% sequence identity to a polynucleotide sequence selected from the group consisting of SEQ ID Nos 1, 3, 5 and 7, wherein the polynucleotides are recombinant or synthetic. Such polynucleotides may be incorporated into a vector such as an expression vector, and said vector may be transformed into a host cell such as a prokaryotic cell for culture, expression and production of the recombinant polymerase. The invention includes or variants and analogues of any of the foregoing.

The invention also encompasses a method for DNA synthesis at high salt concentration, comprising: a) providing a DNA polymerase comprising an amino acid sequence having at least 60% sequence identity to an amino acid sequence selected from the group consisting of SEQ ID Nos 2, 4, 6 and 8, b) contacting a DNA polymerase with a nucleic acid template under conditions of high salt concentration, wherein high salt concentration is defined as ionic conditions of at least 3% salt KCl wt/vol, and c) effecting template dependent synthesis of DNA. Such a method may further comprise contacting a PCR enhancing factor and/or an additive with said DNA polymerase and said nucleic acid template. In such methods the high salt concentration may comprise conditions of between 5% and 25% salt KCl wt/vol.

The invention also encompasses a kit comprising a sequencing reagent for DNA sequencing or amplification, the reagent comprising a high salt tolerant DNA polymerase having at least 60% sequence identity to a polypeptide sequence selected from the group consisting of RD0, RD1, RD2, and RD3.

Further Embodiments and Examples

Identification, isolation, and engineering of high salt tolerant DNA polymerases specifically with a view to nanopore sequencing.

Rationale: A method for boosting signal to noise for ionic-current-based nanopore measurements is to run the assays in higher ionic strength buffers. Although phi29 DNAP can replicate DNA in 0.6 M KCl, the rate of catalysis is slowed two-fold relative to the rate in 0.3 M KCl, and in 1 M KCl there is no detectable binding of the enzyme to DNA substrates (Cherf, unpublished observation). Therefore it is desirable to identify and use salt-adapted polymerases that otherwise share structural and functional properties with phi29 DNAP polymerase.

Among members of the extreme halophiles, salt-tolerance is achieved not by exclusion of monovalent ions from the cytosol, but by adapting intracellular machinery function in elevated salt. As an example of salt tolerance among members of the extreme halophiles, malate dehydrogenase from the archaeal halophile Haloarcula marismortui incorporates a salt-adaptive strategy where the high ionic concentration from the environment is not only tolerated but is incorporated within the protein; sodium and chloride ions are found incorporated within the molecule itself (Richard et al.).

When considering viruses that infect extreme halophiles, not only are proteins of the viral capsid exposed directly to the environment, but the proteins of the replication machinery must operate effectively within the elevated salt environment of its archaeal host.

Purified viral DNA from the halophilic virus His2 is capable of transfecting a wide range of haloarchaeal species (Porter & Dyall-Smith, 2008). Though this may not be environmentally relevant, it does require that proteins of His2 must tolerate the ionic conditions of multiple hosts. The polymerase encoded by His1 and His2 may then not only tolerate high ionic strength but would be expected to properly fold and function in elevated salt.

DNA Polymerases from Salterproviruses His1 and His2.

The inventors have reviewed the literature for viruses of halophilic extremophiles and conducted a sequence homology comparison between phi29 DNAP and DNA and protein sequences of halophilic viruses and archaeal extremophiles. Promising candidates include salterprovirus His1 and His2 (Bath et al. 2006; Prangishvili et al. 2006). His1 and His2 were found to contain a putative single protein DNA polymerase with sequence homology to phi29 DNA polymerase including the TPR2 sub-domain of phi29 DNA polymerase (sub-domain responsible for high level of processivity by 29 DNA polymerase, Rodriguez et al. 2005).

The inventors initially isolated and characterized the DNA polymerase from His1 and His2. Both His1 and His2 viruses and hosts are available through the German Resource Centre for Biological Material (DSMZ). Halophilic archaeal virus alternatives to His1 and His2 were also identified, and include—Hs1, H, Ch1, HF1, HF2, HRPV-1, HHPV-1 and SH1 (Kukkardo, 2008).

Expression and Purification of Proteins from Halophiles and Haloviruses.

Isolation of these proteins can be accomplished using proven expression systems, including *E. coli*. Seryl-tRNA synthetase from Haloarcula marismortui was successfully cloned and overexpressed as a thioredoxin fusion (Taupin et al.). An alternative expression and purification strategy can be employed for halophilic proteins that takes advantage of the increased solubility of halophilic proteins under elevated salt concentration (salting-in), while proteins of the expression host become insoluble (salting out). Folding, stability and subsequent activity of the halophilic protein can then be improved. A third expression strategy makes use of transformation in a halophilic expression host (*Haloferax volcanii*) in order to maintain folding of the protein within the 1-4M KCl presented by the intracellular environment of this host (Plosser & Pfeifer).

Isolation of Novel Haloviruses and Halovirus DNA.

Sampling from extreme environments is limited mainly by safe access to the environment and appropriate authorization permits. In the case of halophilic environments with near-saturating conditions, numerous salt lakes including the Pink lakes of the western United States are known to harbor vast numbers of the Halobacteriaiaceae. Western salt lakes have provided the essential conditions for many halophilic discoveries including Owens lake, the Salton Sea (Swan et al.), Death Valley (Mormile et al.) and the Great salt lake in Utah (Tsai et al., 1995). Additionally, *Halorubrum californiense*, was recently isolated in a solar salt pond near the southern tip of the San Francisco Bay (Pesenti et al.). Viruses of these Haloarchaeal hosts, the haloviruses, outnumber the cellular population by 10-100 fold (Porter et al.), and in some cases, classic plaque assays are possible, as demonstrated by Dyall-Smith and coworkers (Gunde-Cimerman et al.; Stedman et al.).

The invention claimed is:

1. An in vitro method for DNA synthesis at high salt concentration, the method comprising:
   a) providing a DNA polymerase with polymerization activity and having at least 95% sequence identity to an amino acid sequence selected from the group consisting of SEQ ID Nos. 2, 4, 6, and 8,
   b) contacting said DNA polymerase with a nucleic acid template under conditions of high salt concentration, wherein high salt concentration is defined as ionic conditions of at least 3% salt wt/vol, and
   c) effecting template-dependent synthesis of DNA in vitro.

2. The method of claim 1, further comprising contacting a PCR enhancing factor with said DNA polymerase and said nucleic acid template.

3. The method of claim 1, wherein said high salt concentration comprises conditions of between 3% and 25% salt wt/vol.

4. The method of claim 1, wherein said high salt concentration comprises conditions of between 5% and 25% salt wt/vol.

5. The method of claim 1, wherein said high salt concentration comprises conditions of at least 5% salt wt/vol.

6. The method of claim 1, wherein said DNA polymerase has an amino acid sequence selected from the group consisting of SEQ ID Nos. 2, 4, 6, and 8.

7. The method of claim 1 wherein the average rate of polymerization is at least 20 bases per minute.

* * * * *

SEQUENCE LISTING

<160> NUMBER OF SEQ ID NOS: 13

<210> SEQ ID NO 1
<211> LENGTH: 1956
<212> TYPE: DNA
<213> ORGANISM: Unknown
<220> FEATURE:
<223> OTHER INFORMATION: Isolated from a metagenome of viruses of halophilic archaebacteria

<400> SEQUENCE: 1

| | | | | | |
|---|---|---|---|---|---|
| atgagtaaat | ccgacgtccc | gctcgaagcc | attgatacgt | cagctgttca | ccgagacctt | 60 |
| cggaagccga | agtggttagc | gaatgcgtca | atcaccgcta | tggactttga | aacagcggac | 120 |
| ggagaaccgt | ttatgctggc | ggtttcggaa | tccgaccggg | attatgtgat | tgagccgtcg | 180 |
| aaacggaacc | agatactaga | cggggaaaca | ctggtgggaa | cactcgccgc | gtctcggttt | 240 |
| accgggaatc | atattgtcgt | ctggtataat | ctcggctttg | acgcggaaat | ctttacccga | 300 |
| acactcgggg | ccgaagcggc | gaccgagtta | tatttggaga | atcagactga | ataccagaca | 360 |
| gaagacggcc | gaacggtcgg | aattacgtac | attccgggga | agctgctacg | gtttgactta | 420 |
| cccgggaatc | agacggtcga | acactacgat | attggtaaca | tcgttcgtgg | tgggttagaa | 480 |
| tcaggagcga | gagaatggct | cggtgattcc | gtctcgaaag | cgaacgacgg | gctcgaagcg | 540 |
| tctcgattcg | gcgagacgga | ctacagaatc | gataactgga | atgaaatcaa | gcgatacgcc | 600 |
| gaacaggatt | cggtactgac | gcgccgactc | gctcgggctg | ttctctcgaa | agccgaagcg | 660 |
| gtcggtattc | ccgctcgaaa | tccggtgtcg | acgggttcac | tcgccgtctc | atggttagcg | 720 |
| tcagagttag | atacgaaacc | cggttggggc | ccgacaccgg | ttcaatctct | cgcgtgggac | 780 |
| tcattcgctg | gtggtcgctt | cgaggtattc | gagcggggag | ctgttggaga | agtggccgga | 840 |
| cccgacatta | attccgcata | cccggcggtt | atggctggct | tacctgaccc | cgggacgctc | 900 |
| gcgtggaaca | caaccgaatc | agtaactctt | accgacattc | gagacgcgga | ttatggattc | 960 |
| gtccgcgcga | ccgtctcaac | cgattcgtct | cgtcgcattc | agccatttgc | ggtgaaacaa | 1020 |
| gatgaatcg | tcacctatcc | ggcttgtaac | tcggttgaag | taacgacgct | tcgagagacg | 1080 |
| tttatccatg | ctatcgaggc | gggatacgta | acggaatttg | agattagtaa | agtctcactc | 1140 |
| ggttacgaaa | cggacgttac | taactatccg | ttttcgtttc | tcgaaggtgt | gtatgaagag | 1200 |
| agaaaagcgc | tcgaagcgga | cggccgagat | ttggctggac | taatgctgaa | aatcgtgctt | 1260 |
| aactcgttgt | atggaaagac | cgcccaaacg | actctcaagc | ggtcggtgat | tcgagacgag | 1320 |
| attagtccgt | ccgaagcggc | cgccgaatcg | catgagcggt | tcaagtcgct | cgaaggaatc | 1380 |
| ccatacgtgg | aaagtcaaga | agcgggctcg | ctgttcaatc | cgtttatcgc | gtcgtatatc | 1440 |
| actggtaaaa | caagactcga | attacacaag | tcaatcaccg | agacggagct | cgaaaatgat | 1500 |
| actgtcatgt | tcgctacgga | ctgtataatg | attcatgcgg | acgcttacga | tgaatctgac | 1560 |
| tttgacagtc | gcttaggcga | tacactcggt | gaatgggaat | ttgattatcg | aggagacgcg | 1620 |
| ttcgtagttg | gttctggtgt | gtatgaagtt | gataccggag | acggactcaa | gatgggaacg | 1680 |
| cgtgggttcc | gagaagcgag | tttcgagtcc | cttcgagaaa | ccgcgtctaa | cgccactgac | 1740 |
| gggattccgc | ttgaaacgac | ccgtcccgta | acactcggtg | aagcggtcgc | tagggggtcc | 1800 |
| agttatagcc | tttcagatat | tggtgaattt | cttacgtcgt | ctcggaatct | tcaaccggac | 1860 |
| tttgaccgga | aacagagcgtg | ggacgaatcg | ccgtcgttcc | gagagttgac | cgagcgttcg | 1920 |
| ttttacggcc | cgcccccggat | tctcgaaggc | aactag | | | 1956 |

<210> SEQ ID NO 2
<211> LENGTH: 651
<212> TYPE: PRT
<213> ORGANISM: Unknown
<220> FEATURE:
<223> OTHER INFORMATION: Isolated from a metagenome of viruses of halophilic archaebacteria

<400> SEQUENCE: 2

Met Ser Lys Ser Asp Val Pro Leu Glu Ala Ile Asp Thr Ser Ala Val
1               5                   10                  15

His Arg Asp Leu Arg Lys Pro Lys Trp Leu Ala Asn Ala Ser Ile Thr
            20                  25                  30

Ala Met Asp Phe Glu Thr Ala Asp Gly Glu Pro Phe Met Leu Ala Val
        35                  40                  45

Ser Glu Ser Asp Arg Asp Tyr Val Ile Glu Pro Ser Lys Arg Asn Gln
    50                  55                  60

Ile Leu Asp Gly Glu Thr Leu Val Gly Thr Leu Ala Ala Ser Arg Phe
65                  70                  75                  80

Thr Gly Asn His Ile Val Val Trp Tyr Asn Leu Gly Phe Asp Ala Glu
                85                  90                  95

Ile Phe Thr Arg Thr Leu Gly Ala Glu Ala Ala Thr Glu Leu Tyr Leu
            100                 105                 110

Glu Asn Gln Thr Glu Tyr Gln Thr Glu Asp Gly Arg Thr Val Gly Ile
        115                 120                 125

Thr Tyr Ile Pro Gly Lys Leu Leu Arg Phe Asp Leu Pro Gly Asn Gln
    130                 135                 140

Thr Val Glu His Tyr Asp Ile Gly Asn Ile Val Arg Gly Gly Leu Glu
145                 150                 155                 160

Ser Gly Ala Arg Glu Trp Leu Gly Asp Ser Val Ser Lys Ala Asn Asp
                165                 170                 175

Gly Leu Glu Ala Ser Arg Phe Gly Glu Thr Asp Tyr Arg Ile Asp Asn
            180                 185                 190

Trp Asn Glu Ile Lys Arg Tyr Ala Glu Gln Asp Ser Val Leu Thr Arg
        195                 200                 205

Arg Leu Ala Arg Ala Val Leu Ser Lys Ala Glu Ala Val Gly Ile Pro
    210                 215                 220

Ala Arg Asn Pro Val Ser Thr Gly Ser Leu Ala Val Ser Trp Leu Ala
225                 230                 235                 240

Ser Glu Leu Asp Thr Lys Pro Gly Trp Gly Pro Thr Pro Val Gln Ser
                245                 250                 255

Leu Ala Trp Asp Ser Phe Ala Gly Gly Arg Phe Glu Val Phe Glu Arg
            260                 265                 270

Gly Ala Val Gly Glu Val Ala Gly Pro Asp Ile Asn Ser Ala Tyr Pro
        275                 280                 285

Ala Val Met Ala Gly Leu Pro Asp Pro Gly Thr Leu Ala Trp Asn Thr
    290                 295                 300

Thr Glu Ser Val Thr Leu Thr Asp Ile Arg Asp Ala Asp Tyr Gly Phe
305                 310                 315                 320

Val Arg Ala Thr Val Ser Thr Asp Ser Ser Arg Arg Ile Gln Pro Phe
                325                 330                 335

Ala Val Lys Gln Asp Gly Ile Val Thr Tyr Pro Ala Cys Asn Ser Val
            340                 345                 350

Glu Val Thr Thr Leu Arg Glu Thr Phe Ile His Ala Ile Glu Ala Gly
        355                 360                 365

```
Tyr Val Thr Glu Phe Glu Ile Ser Lys Val Ser Leu Gly Tyr Glu Thr
        370                 375                 380

Asp Val Thr Asn Tyr Pro Phe Ser Phe Leu Glu Gly Val Tyr Glu Glu
385                 390                 395                 400

Arg Lys Ala Leu Glu Ala Asp Gly Arg Asp Leu Ala Gly Leu Met Leu
                405                 410                 415

Lys Ile Val Leu Asn Ser Leu Tyr Gly Lys Thr Ala Gln Thr Thr Leu
                420                 425                 430

Lys Arg Ser Val Ile Arg Asp Glu Ile Ser Pro Ser Glu Ala Ala Ala
                435                 440                 445

Glu Ser His Glu Arg Phe Lys Ser Leu Glu Gly Ile Pro Tyr Val Glu
        450                 455                 460

Ser Gln Glu Ala Gly Ser Leu Phe Asn Pro Phe Ile Ala Ser Tyr Ile
465                 470                 475                 480

Thr Gly Lys Thr Arg Leu Glu Leu His Lys Ser Ile Thr Glu Thr Glu
                485                 490                 495

Leu Glu Asn Asp Thr Val Met Phe Ala Thr Asp Cys Ile Met Ile His
                500                 505                 510

Ala Asp Ala Tyr Asp Glu Ser Asp Phe Asp Ser Arg Leu Gly Asp Thr
        515                 520                 525

Leu Gly Glu Trp Glu Phe Asp Tyr Arg Gly Asp Ala Phe Val Val Gly
530                 535                 540

Ser Gly Val Tyr Glu Val Asp Thr Gly Asp Gly Leu Lys Met Gly Thr
545                 550                 555                 560

Arg Gly Phe Arg Glu Ala Ser Phe Glu Ser Leu Arg Glu Thr Ala Ser
                565                 570                 575

Asn Ala Thr Asp Gly Ile Pro Leu Glu Thr Thr Arg Pro Val Thr Leu
                580                 585                 590

Gly Glu Ala Val Ala Arg Gly Ser Ser Tyr Ser Leu Ser Asp Ile Gly
        595                 600                 605

Glu Phe Leu Thr Ser Ser Arg Asn Leu Gln Pro Asp Phe Asp Arg Lys
610                 615                 620

Arg Ala Trp Asp Glu Ser Pro Ser Phe Arg Glu Leu Thr Glu Arg Ser
625                 630                 635                 640

Phe Tyr Gly Pro Pro Arg Ile Leu Glu Gly Asn
                645                 650

<210> SEQ ID NO 3
<211> LENGTH: 2199
<212> TYPE: DNA
<213> ORGANISM: Unknown
<220> FEATURE:
<223> OTHER INFORMATION: Isolated from a metagenome of viruses of
      halophilic archaebacteria

<400> SEQUENCE: 3
atgtctaaat cagacattcc attatctgat ttagatatta ctaaggcggt tcaaacccaa      60
aacaaagcaa agttcaaaga agataaacaa atcaatgcgt ttgatacaga aacgtcgaat     120
gggagtgtgt ttatggtatc ttacgcattt gaaaaaatgt ctggtgttat tgattcgggt     180
agtacggaag aattgtcaag taagaaaatt tggaatttac taacttattc cgggtgtcgt     240
gaagcaatta acgtatggta taacttagac tttgacgcaa atgcgctttt atctggttta     300
cttgataatg acgacttgtg taaacttgta gtaaaaaata gagtgacaac aaaaatacgt     360
gaacataaat tcgcaataac atatgtaaaa agcaaatttc taagtattaa gaatttggac     420
```

-continued

```
acaaatcacc gtttcgatca ttacgatatt gcccaatact tctatacatc attaaatgat    480
gcagcgaatg agtggataga tgaagaaaag aaaggggaa tagatacaac aatgttcgga     540
aaaagcgttt gttcagaaca tactaaacaa gcattaaata agaaattga accacaaccg     600
aaagacgaat gttcagaatg tgtaactaaa gaagaagcga acgaatatgt taattctaac   660
tatgaacaaa taagagaata tgccgaaaaa gatgcggcag tcacaaagaa attagctgtt   720
gcattgttca atgaaggaga gaggctaaat attcccttg aaaaccgtt ttcgactgga     780
tggttgtcgg cagaatatca aagagccaat acagaacaaa gcctaactt tggaaacaaa    840
gacattcagg cttattttg ggaaagttat cacggcggta gatttgaagt atttgaacgt    900
ggaaatgtcg gtgaagttgt tggtccagat attaattcag catatccggc aattatggca   960
aagttacccg cacctactac attagactgg cggattgttg gtaattatga aatgagggga  1020
catacgtttg attttgaaaa tattaaagaa tgtgattatg gtgttgtgag agtgaatgtg  1080
tcaacagata gtagtaggaa atacaaccg tttgctttca aaatcaatgc tgtaacatca   1140
tatccctcat ttaacgatac ggaataatt gtcttgaaag atattttga atttgcggta    1200
aagaatggat tagttacaga ttacaaatta ttagacggat attaggata tgaaaccgaa   1260
cggacggaat acccatttag ttggattgcc gatttgtatg ccgaacggaa agttagtgaa  1320
aagttgcaca atttgaaaaa gaagccaaa ctgttgaaaa ttgtgttaaa ttcagcttat    1380
gggaaaacgt gtcaaactac aactaagaaa agattgatga aactggggga agatgaaaca  1440
tatacattag aagataatga acgtttgtat cctaaagatt atcttagtaa aatgcaacga  1500
gaatacatat ctgataatac gcttatcatt gaaactaatt ccgccggaaa acgatttaat  1560
cctttctttg cttcatacat tacgggatta acacggttag aattgcataa acgtgtaatg  1620
gaatataatc tgatagatga tacgtatatg tttgctactg attgtataat ggtagacaaa  1680
cgtgcatatg aacaaagtaa ttttgagtct gttgttcagg tggcggatga ttcacttgaa  1740
gaaaaacaat tcgtaaaat ggcaaaagat agcttaggaa tgtgggactt tgattattca   1800
ggaaatgcgt ttattgttgg ttcaggagtt tacgaaattg tcttaccaa tggtgatata    1860
aaaacaaaga cgcgaggatt tacaaatggt gcattagacg gacaattagt tgaaatggca  1920
aataaacacc caaacggaat accgcttgaa aacaaccgcc caataacatt aggtgaaatg  1980
ttccagaatc cggaaattgg taatgttgca tcattcacaa aacaatggaa agagttaaag  2040
ccaaactttg attcaaaacg taattgggat atttctaatc catcatttat tgatttgtta  2100
gataattcgc attgcagttc cccattgcgt gtaaatgaaa atacgaaata tacgaatgaa  2160
gaaattgtcg tttcccaaat ttcaggaatt ggaggataa                          2199
```

<210> SEQ ID NO 4
<211> LENGTH: 732
<212> TYPE: PRT
<213> ORGANISM: Unknown
<220> FEATURE:
<223> OTHER INFORMATION: Isolated from a metagenome of viruses of
      halophilic archaebacteria

<400> SEQUENCE: 4

Met Ser Lys Ser Asp Ile Pro Leu Ser Asp Leu Asp Ile Thr Lys Ala
1               5                   10                  15

Val Gln Thr Gln Asn Lys Ala Lys Phe Lys Glu Asp Lys Gln Ile Asn
            20                  25                  30

Ala Phe Asp Thr Glu Thr Ser Asn Gly Ser Val Phe Met Val Ser Tyr

-continued

```
                35                  40                  45
Ala Phe Glu Lys Met Ser Gly Val Ile Asp Ser Gly Ser Thr Glu Glu
 50                  55                  60

Leu Ser Ser Lys Lys Ile Trp Asn Leu Leu Thr Tyr Ser Gly Cys Arg
 65                  70                  75                  80

Glu Ala Ile Asn Val Trp Tyr Asn Leu Asp Phe Asp Ala Asn Ala Leu
                     85                  90                  95

Leu Ser Gly Leu Leu Asp Asn Asp Leu Cys Lys Leu Val Val Lys
                100                 105                 110

Asn Arg Val Thr Thr Lys Ile Arg Glu His Lys Phe Ala Ile Thr Tyr
                115                 120                 125

Val Lys Ser Lys Phe Leu Ser Ile Lys Asn Leu Asp Thr Asn His Arg
                130                 135                 140

Phe Asp His Tyr Asp Ile Ala Gln Tyr Phe Tyr Thr Ser Leu Asn Asp
145                 150                 155                 160

Ala Ala Asn Glu Trp Ile Asp Glu Glu Lys Lys Gly Gly Ile Asp Thr
                    165                 170                 175

Thr Met Phe Gly Lys Ser Val Cys Ser Glu His Thr Lys Gln Ala Leu
                180                 185                 190

Asn Lys Glu Ile Glu Pro Gln Pro Lys Asp Glu Cys Ser Glu Cys Val
                195                 200                 205

Thr Lys Glu Glu Ala Asn Glu Tyr Val Asn Ser Asn Tyr Glu Gln Ile
210                 215                 220

Arg Glu Tyr Ala Glu Lys Asp Ala Ala Val Thr Lys Lys Leu Ala Val
225                 230                 235                 240

Ala Leu Phe Asn Glu Gly Arg Leu Asn Ile Pro Phe Gly Lys Pro
                    245                 250                 255

Phe Ser Thr Gly Trp Leu Ser Ala Glu Tyr Gln Arg Ala Asn Thr Glu
                260                 265                 270

Gln Lys Pro Asn Phe Gly Asn Lys Asp Ile Gln Ala Tyr Phe Trp Glu
                275                 280                 285

Ser Tyr His Gly Gly Arg Phe Glu Val Phe Glu Arg Gly Asn Val Gly
                290                 295                 300

Glu Val Val Gly Pro Asp Ile Asn Ser Ala Tyr Pro Ala Ile Met Ala
305                 310                 315                 320

Lys Leu Pro Ala Pro Thr Thr Leu Asp Trp Arg Ile Val Gly Asn Tyr
                    325                 330                 335

Asp Asn Glu Gly His Thr Phe Asp Phe Glu Asn Ile Lys Glu Cys Asp
                340                 345                 350

Tyr Gly Val Val Arg Val Asn Val Ser Thr Asp Ser Ser Arg Lys Ile
                355                 360                 365

Gln Pro Phe Ala Phe Lys Ile Asn Ala Val Thr Ser Tyr Pro Ser Phe
                370                 375                 380

Asn Asp Thr Glu Ile Ile Val Leu Lys Asp Ile Phe Glu Phe Ala Val
385                 390                 395                 400

Lys Asn Gly Leu Val Thr Asp Tyr Lys Leu Leu Asp Gly Tyr Leu Gly
                    405                 410                 415

Tyr Glu Thr Glu Arg Thr Glu Tyr Pro Phe Ser Trp Ile Ala Asp Leu
                420                 425                 430

Tyr Ala Glu Arg Lys Val Ser Glu Lys Leu His Asn Leu Lys Lys Lys
                435                 440                 445

Ala Lys Leu Leu Lys Ile Val Leu Asn Ser Ala Tyr Gly Lys Thr Cys
450                 455                 460
```

Gln Thr Thr Thr Lys Lys Arg Leu Met Lys Leu Gly Glu Asp Glu Thr
465                 470                 475                 480

Tyr Thr Leu Glu Asp Asn Glu Arg Leu Tyr Pro Lys Asp Tyr Leu Ser
            485                 490                 495

Lys Met Gln Arg Glu Tyr Ile Ser Asp Asn Thr Leu Ile Ile Glu Thr
        500                 505                 510

Asn Ser Ala Gly Lys Arg Phe Asn Pro Phe Ala Ser Tyr Ile Thr
    515                 520                 525

Gly Leu Thr Arg Leu Glu Leu His Lys Arg Val Met Glu Tyr Asn Leu
530                 535                 540

Ile Asp Asp Thr Tyr Met Phe Ala Thr Asp Cys Ile Met Val Asp Lys
545                 550                 555                 560

Arg Ala Tyr Glu Gln Ser Asn Phe Glu Ser Val Val Gln Val Ala Asp
                565                 570                 575

Asp Ser Leu Glu Glu Lys Gln Phe Arg Lys Met Ala Lys Asp Ser Leu
            580                 585                 590

Gly Met Trp Asp Phe Asp Tyr Ser Gly Asn Ala Phe Ile Val Gly Ser
        595                 600                 605

Gly Val Tyr Glu Ile Val Leu Pro Asn Gly Asp Ile Lys Thr Lys Thr
    610                 615                 620

Arg Gly Phe Thr Asn Gly Ala Leu Asp Gly Gln Leu Val Glu Met Ala
625                 630                 635                 640

Asn Lys His Pro Asn Gly Ile Pro Leu Glu Asn Asn Arg Pro Ile Thr
                645                 650                 655

Leu Gly Glu Met Phe Gln Asn Pro Glu Ile Gly Asn Val Ala Ser Phe
            660                 665                 670

Thr Lys Gln Trp Lys Glu Leu Lys Pro Asn Phe Asp Ser Lys Arg Asn
        675                 680                 685

Trp Asp Ile Ser Asn Pro Ser Phe Ile Asp Leu Leu Asp Asn Ser His
    690                 695                 700

Cys Ser Ser Pro Leu Arg Val Asn Glu Asn Thr Lys Tyr Thr Asn Glu
705                 710                 715                 720

Glu Ile Val Val Ser Gln Ile Ser Gly Ile Gly Gly
                725                 730

<210> SEQ ID NO 5
<211> LENGTH: 2016
<212> TYPE: DNA
<213> ORGANISM: Unknown
<220> FEATURE:
<223> OTHER INFORMATION: Isolated from a metagenome of viruses of
      halophilic archaebacteria

<400> SEQUENCE: 5
atgagtaagt ccgatagcga cctttccgaa attgacacta gcagggtaac gacgaagact      60
agaagtatta acctgaaaga acctagcagg attaacgctt tcgacaccga aacagcggac     120
ggtagaatct ttttggttag ttacgacttt gaaggtgccg aaagtggtgt cttcggaaag     180
aaagacggct tcgttaaccc gtctaagcta tgggatttac ttaccgatta caaatgtaga     240
aatgcacaaa atatgtggta taatcttagc ttcgatagcg acgttttcct ttcgtcggtg     300
ctagccccag acgaagttac ggagttagca gtaaaaggat cggtagaagc tagggggctac     360 gaaatagtgt atattccggg taagttttg aagattaccg acgaaaataa gcatacatat     420
acccactatg acgccgccca gttttctat gatagtctag acggtgccgc tagtgagtgg     480

```
ctaggagaaa ataagacggc aggtgtcaat actgaaaggt ttggcaaaga cggtatgaaa     540
cctaacgaat atatcaggga taactttagg gacattaaaa tctatgccga aaaagacgct    600
aagttaaccc gtaagttgtg gcgtaagctt acgtcgaaag cggttagttt agatattccg    660
attagtaagc cgattagtac cggttactta gctcaagaat ggatggatta ccacctacca    720
catagacccg gcttcggacc taccgaaatg caaagtttag catgggatag ttacgctggg    780
ggtaggtttg aagtatttga aaggggtaac gtcggtagcg taatcggtgc cgatattaat    840
agtgcatacc ctaacgtctt agctaatcta cctgatccta gtacccttcg gtgggaaagg    900
gtagaaaacc caagctttca ggaattagca ggtgccgatt atgggtttgt aaacgctacc    960
gtaactaccg ataggagtaa aagaatccaa cctttcgcta tgaaagtaga cgacgtagtg   1020
aaatacccgg cactaaaaca ggtagaaatt aatacccctgc tagatatatt taccttcgct  1080
aagtctaacg ggtatttgat cgaagatacg gttaacgaag cttggttagg atacgaaact   1140
aacgggacga aaaggccgtt tggtgaaatc cctgaaatgt atgatagtcg taagaccgcc   1200
gaagctaacg gtaaatgaa acaggggtta ctactaaaaa tcatccttaa ttctatgtat    1260
ggtaaattct gccaaaccac ccctaagagg gaatacttag aggaaactaa gaacctgaaa   1320
gattacgagg aaatagtacc cggcatttcc ctacctgcta gcatacgcga aacgctaaaa   1380
gacgaagtga tcgaaaggtt agaagccggt ccatacttta atccgtttat ggctagctac   1440
attaccggta tgactaggct acaattacac aaatcggtag aaaagcatga tttggtagaa   1500
gatactatta tgttcgctac cgattgcatc atggtagaag ccgacgcttt ccgtaggagt   1560
aacttcgacc tagtagacga aagcttacca tacgctaaac agctaggtgg gtgggataag   1620
gaatatgaag gccatgctaa cgtaatcggt gccggtgtct atgaggtaga catgggcgat   1680
aagactaaga ccatgactag gggctttagg gaaaaggatt tagacaccat ttccctagtg   1740
aaagaggtta agaaaacgg tggaattaca gcaaatacta accggcctat gacgctaaag    1800
gaagccgtat ggcatgggcg gcctattagc gacgtagggg cgtttagtga tagcgatagg   1860
aagatagacc ctaatatgga tgaaaagcgt gtatggccta atgagctaac ttggcagggt   1920
ttcatagacg aaagacaggt aggtaatcct ttgctattag acgatagtga aaatgacgaa   1980
gatagtggta gtaaatcggt agctataagt gggtag                             2016
```

<210> SEQ ID NO 6  
<211> LENGTH: 671  
<212> TYPE: PRT  
<213> ORGANISM: Unknown  
<220> FEATURE:  
<223> OTHER INFORMATION: Isolated from a metagenome of viruses of halophilic archaebacteria

<400> SEQUENCE: 6

```
Met Ser Lys Ser Asp Ser Asp Leu Ser Glu Ile Asp Thr Ser Arg Val
1               5                   10                  15

Thr Thr Lys Thr Arg Ser Ile Asn Leu Lys Glu Pro Ser Arg Ile Asn
            20                  25                  30

Ala Phe Asp Thr Glu Thr Ala Asp Gly Arg Ile Phe Leu Val Ser Tyr
        35                  40                  45

Asp Phe Glu Gly Ala Glu Ser Gly Val Phe Gly Lys Lys Asp Gly Phe
    50                  55                  60

Val Asn Pro Ser Lys Leu Trp Asp Leu Leu Thr Asp Tyr Lys Cys Arg
65                  70                  75                  80

Asn Ala Gln Asn Met Trp Tyr Asn Leu Ser Phe Asp Ser Asp Val Phe
```

-continued

```
                    85                  90                  95
Leu Ser Ser Val Leu Ala Pro Asp Glu Val Thr Glu Leu Ala Val Lys
                100                 105                 110

Gly Ser Val Glu Ala Arg Gly Tyr Glu Ile Val Tyr Ile Pro Gly Lys
                115                 120                 125

Phe Leu Lys Ile Thr Asp Glu Asn Lys His Thr Tyr Thr His Tyr Asp
                130                 135                 140

Ala Ala Gln Phe Phe Tyr Asp Ser Leu Asp Gly Ala Ala Ser Glu Trp
145                 150                 155                 160

Leu Gly Glu Asn Lys Thr Ala Gly Val Asn Thr Glu Arg Phe Gly Lys
                165                 170                 175

Asp Gly Met Lys Pro Asn Glu Tyr Ile Arg Asp Asn Phe Arg Asp Ile
                180                 185                 190

Lys Ile Tyr Ala Glu Lys Asp Ala Lys Leu Thr Arg Lys Leu Trp Arg
                195                 200                 205

Lys Leu Thr Ser Lys Ala Val Ser Leu Asp Ile Pro Ile Ser Lys Pro
                210                 215                 220

Ile Ser Thr Gly Tyr Leu Ala Gln Glu Trp Met Asp Tyr His Leu Pro
225                 230                 235                 240

His Arg Pro Gly Phe Gly Pro Thr Glu Met Gln Ser Leu Ala Trp Asp
                245                 250                 255

Ser Tyr Ala Gly Gly Arg Phe Glu Val Phe Glu Arg Gly Asn Val Gly
                260                 265                 270

Ser Val Ile Gly Ala Asp Ile Asn Ser Ala Tyr Pro Asn Val Leu Ala
                275                 280                 285

Asn Leu Pro Asp Pro Ser Thr Leu Arg Trp Glu Arg Val Glu Asn Pro
                290                 295                 300

Ser Phe Gln Glu Leu Ala Gly Ala Asp Tyr Gly Phe Val Asn Ala Thr
305                 310                 315                 320

Val Thr Thr Asp Arg Ser Lys Arg Ile Gln Pro Phe Ala Met Lys Val
                325                 330                 335

Asp Asp Val Val Lys Tyr Pro Ala Leu Lys Gln Val Glu Ile Asn Thr
                340                 345                 350

Leu Leu Asp Ile Phe Thr Phe Ala Lys Ser Asn Gly Tyr Leu Ile Glu
                355                 360                 365

Asp Thr Val Asn Glu Ala Trp Leu Gly Tyr Glu Thr Asn Gly Thr Lys
                370                 375                 380

Arg Pro Phe Gly Glu Ile Pro Glu Met Tyr Asp Ser Arg Lys Thr Ala
385                 390                 395                 400

Glu Ala Asn Gly Lys Met Lys Gln Gly Leu Leu Leu Lys Ile Ile Leu
                405                 410                 415

Asn Ser Met Tyr Gly Lys Phe Cys Gln Thr Thr Pro Lys Arg Glu Tyr
                420                 425                 430

Leu Glu Glu Thr Lys Asn Leu Lys Asp Tyr Glu Glu Ile Val Pro Gly
                435                 440                 445

Ile Ser Leu Pro Ala Ser Ile Arg Glu Thr Leu Lys Asp Glu Val Ile
                450                 455                 460

Glu Arg Leu Glu Ala Gly Pro Tyr Phe Asn Pro Phe Met Ala Ser Tyr
465                 470                 475                 480

Ile Thr Gly Met Thr Arg Leu Gln Leu His Lys Ser Val Glu Lys His
                485                 490                 495

Asp Leu Val Glu Asp Thr Ile Met Phe Ala Thr Asp Cys Ile Met Val
                500                 505                 510
```

```
Glu Ala Asp Ala Phe Arg Arg Ser Asn Phe Asp Leu Val Asp Glu Ser
            515                 520                 525
Leu Pro Tyr Ala Lys Gln Leu Gly Gly Trp Asp Lys Glu Tyr Glu Gly
        530                 535                 540
His Ala Asn Val Ile Gly Ala Gly Val Tyr Glu Val Asp Met Gly Asp
545                 550                 555                 560
Lys Thr Lys Thr Met Thr Arg Gly Phe Arg Glu Lys Asp Leu Asp Thr
                565                 570                 575
Ile Ser Leu Val Lys Glu Val Lys Gly Asn Gly Ile Thr Ala Asn
            580                 585                 590
Thr Asn Arg Pro Met Thr Leu Lys Glu Ala Val Trp His Gly Arg Pro
        595                 600                 605
Ile Ser Asp Val Gly Ala Phe Ser Asp Ser Asp Arg Lys Ile Asp Pro
    610                 615                 620
Asn Met Asp Glu Lys Arg Val Trp Pro Asn Glu Leu Thr Trp Gln Gly
625                 630                 635                 640
Phe Ile Asp Glu Arg Gln Val Gly Asn Pro Leu Leu Asp Asp Ser
                645                 650                 655
Glu Asn Asp Glu Asp Ser Gly Ser Lys Ser Val Ala Ile Ser Gly
            660                 665                 670

<210> SEQ ID NO 7
<211> LENGTH: 2097
<212> TYPE: DNA
<213> ORGANISM: Unknown
<220> FEATURE:
<223> OTHER INFORMATION: Isolated from a metagenome of viruses of
      halophilic archaebacteria

<400> SEQUENCE: 7
atgtcgaaat ccgatacgcc ggtcgaacta atcgataccg accgggcgag aaagcccctc      60
ggggaagccg atttcgcagg ggatacgccg atagcggcct tagattcgga aacgccgac     120
ggcgatatct tcgccctcgg cgtctattac gccgattccg aggaataccg gcaaatcgta     180
aagaccgacg aaacgataga cggcttagag gttctgaact tcttaacgtc tgacggtatg     240
cgaaattcga taaacgtctg gtttaacctg aatttcgacg ctaatgtaat cctgaaggcc     300
cttccgaggg aaaatcttca ggatatccgg gttcataatt cgacggattt cgagatagac     360
ggtaagacct tcgagattac gtatattccg aagaaatgcc ttcggatttc cgacgggaac     420
gggaacgcct acgaccatta cgacgcttcg cagtttacgt atgcgggcgg cttagaagat     480
tccgccgagg catggttagg cgtagacgac ggcaaagaga acgacgacgt agacgtagaa     540
cggttcggcc tgaacgacga cgggaacccg aacgactaca tagccgagaa agaggctaag     600
attcggcggt atctacgggt agactgtcgg cttacggccg aaatcttcga ggaaatcgtt     660
cgtaccgccg agaacgacgt agaccccgct attcccttcg gaaagccgtt cagtaccggc     720
tacgtagcgg ccgactacat tcggaaccgt accgaatata agccggggta ttcctcggaa     780
gccgttcagt cggcggcatg gaaaacgtac cggggcggcc gcttcgaggt agttaaacgg     840
ggccatgtcg gggacgtagc ggggcctgat attaactcgg cctacccggc cgtcatgtcg     900
gaactacccg acccttctac cctcgaatgg acgctatacg gcgaagggaa ccgccgtcgg     960
gcggcttccg acctatcgct ttccgacgtt cgggattacg attatggctt tctgaaggtt    1020
cgggttacga ccgacgaatc ccggccggtt caacccttcg cagtaaagaa tccgaatgag    1080
ggcggccggg tagaatatcc ggccgtagac gacgccgtag tatgggttct gaaggacatt    1140
```

-continued

```
ttcgagtatg ccgaagccga gggcttcatt accgactacg acgttcaggc cgccgttctc    1200
ggccgagaaa ccgacgctac gaaatacccg ttcggcttct ttaaagacct atacgaccgg    1260
cgaaagaccc tcgaagataa cgaccggggc cgaccggcga aactactgaa aatagtaatg    1320
aacagtatct acgggaaaac ctgtcagacg acggttaacc atgtcgaacc cggcgaattt    1380
atggaaaacg ccgacggctt cgaggatgga aaactgcgaa acaggatat tcccgagggc     1440
tacgacttag taaccgacca tagagggaag ccctacctcg aatatcagtc ggcgggccga    1500
ctgtttaatc ccttcctcgc tacgtacatt accggccgaa cccggctaaa actgttccgg    1560
ggcgtcgtag ataataacct cgaaaacgac gttattatgc tcgctaccga ctgtctaatg    1620
ttcgaccggg aagccttcga gggaaccgac ctacatacgg ccgccgaagc cgaccccgac    1680
gactacgccg acgccctcgg gggatgggat tacgattatg tcggggacgc tttcgtagtc    1740
ggttcgggta tctatcaggt agaccgctac gataaagacg aaacgaaaat gggccttcgg    1800
ggctttaaag acttctactc ggatagtaac gatttcgata cgcttcggga agcggccgag    1860
gaatacgccg acggcggaat cccggttacg actactcggc ccgtaaccta cggcgatatt    1920
ctacataagg gcggtaaact gtcggaaatc ggccggttca gggaatcgga acgaacgctt    1980
tcggccgaca tggatacgaa acgccgatgg aatcgaaccg gggcgtcgtt cgggcggcta    2040
ctcgaaggcc ccgaggggtc ggccccgaaa gtctacgacg gggaagccct cgaataa      2097
```

<210> SEQ ID NO 8
<211> LENGTH: 698
<212> TYPE: PRT
<213> ORGANISM: Unknown
<220> FEATURE:
<223> OTHER INFORMATION: Isolated from a metagenome of viruses of
      halophilic archaebacteria

<400> SEQUENCE: 8

```
Met Ser Lys Ser Asp Thr Pro Val Glu Leu Ile Asp Thr Asp Arg Ala
1               5                   10                  15

Arg Lys Pro Leu Gly Glu Ala Asp Phe Ala Gly Asp Thr Pro Ile Ala
            20                  25                  30

Ala Leu Asp Ser Glu Thr Ala Asp Gly Asp Ile Phe Ala Leu Gly Val
        35                  40                  45

Tyr Tyr Ala Asp Ser Glu Glu Tyr Arg Gln Ile Val Lys Thr Asp Glu
    50                  55                  60

Thr Ile Asp Gly Leu Glu Val Leu Asn Phe Leu Thr Ser Asp Gly Met
65                  70                  75                  80

Arg Asn Ser Ile Asn Val Trp Phe Asn Leu Asn Phe Asp Ala Asn Val
                85                  90                  95

Ile Leu Lys Ala Leu Pro Arg Glu Asn Leu Gln Asp Ile Arg Val His
            100                 105                 110

Asn Ser Thr Asp Phe Glu Ile Asp Gly Lys Thr Phe Glu Ile Thr Tyr
        115                 120                 125

Ile Pro Lys Lys Cys Leu Arg Ile Ser Asp Gly Asn Gly Asn Ala Tyr
    130                 135                 140

Asp His Tyr Asp Ala Ser Gln Phe Thr Tyr Ala Gly Gly Leu Glu Asp
145                 150                 155                 160

Ser Ala Glu Ala Trp Leu Gly Val Asp Gly Lys Glu Asn Asp Asp
                165                 170                 175

Val Asp Val Glu Arg Phe Gly Leu Asn Asp Asp Gly Asn Pro Asn Asp
            180                 185                 190
```

-continued

Tyr Ile Ala Glu Lys Glu Ala Lys Ile Arg Arg Tyr Leu Arg Val Asp
        195                 200                 205

Cys Arg Leu Thr Ala Glu Ile Phe Glu Glu Ile Val Arg Thr Ala Glu
        210                 215                 220

Asn Asp Val Asp Pro Ala Ile Pro Phe Gly Lys Pro Phe Ser Thr Gly
225                 230                 235                 240

Tyr Val Ala Ala Asp Tyr Ile Arg Asn Arg Thr Glu Tyr Lys Pro Gly
                245                 250                 255

Tyr Ser Ser Glu Ala Val Gln Ser Ala Ala Trp Lys Thr Tyr Arg Gly
            260                 265                 270

Gly Arg Phe Glu Val Val Lys Arg Gly His Val Gly Asp Val Ala Gly
        275                 280                 285

Pro Asp Ile Asn Ser Ala Tyr Pro Ala Val Met Ser Glu Leu Pro Asp
        290                 295                 300

Pro Ser Thr Leu Glu Trp Thr Leu Tyr Gly Glu Gly Asn Arg Arg Arg
305                 310                 315                 320

Ala Ala Ser Asp Leu Ser Leu Ser Asp Val Arg Asp Tyr Asp Tyr Gly
                325                 330                 335

Phe Leu Lys Val Arg Val Thr Thr Asp Glu Ser Arg Pro Val Gln Pro
        340                 345                 350

Phe Ala Val Lys Asn Pro Asn Glu Gly Gly Arg Val Glu Tyr Pro Ala
        355                 360                 365

Val Asp Asp Ala Val Val Trp Val Leu Lys Asp Ile Phe Glu Tyr Ala
        370                 375                 380

Glu Ala Glu Gly Phe Ile Thr Asp Tyr Asp Val Gln Ala Ala Val Leu
385                 390                 395                 400

Gly Arg Glu Thr Asp Ala Thr Lys Tyr Pro Phe Gly Phe Phe Lys Asp
                405                 410                 415

Leu Tyr Asp Arg Arg Lys Thr Leu Glu Asp Asn Asp Arg Gly Arg Pro
        420                 425                 430

Ala Lys Leu Leu Lys Ile Val Met Asn Ser Ile Tyr Gly Lys Thr Cys
        435                 440                 445

Gln Thr Thr Val Asn His Val Glu Pro Gly Gly Phe Met Glu Asn Ala
        450                 455                 460

Asp Gly Phe Glu Asp Gly Lys Leu Arg Lys Gln Asp Ile Pro Glu Gly
465                 470                 475                 480

Tyr Asp Leu Val Thr Asp His Arg Gly Lys Pro Tyr Leu Glu Tyr Gln
                485                 490                 495

Ser Ala Gly Arg Leu Phe Asn Pro Phe Leu Ala Thr Tyr Ile Thr Gly
            500                 505                 510

Arg Thr Arg Leu Lys Leu Phe Arg Gly Val Val Asp Asn Asn Leu Glu
        515                 520                 525

Asn Asp Val Ile Met Leu Ala Thr Asp Cys Leu Met Phe Asp Arg Glu
530                 535                 540

Ala Phe Glu Gly Thr Asp Leu His Thr Ala Ala Glu Ala Asp Pro Asp
545                 550                 555                 560

Asp Tyr Ala Asp Ala Leu Gly Gly Trp Asp Tyr Asp Tyr Val Gly Asp
                565                 570                 575

Ala Phe Val Val Gly Ser Gly Ile Tyr Gln Val Asp Arg Tyr Asp Lys
            580                 585                 590

Asp Glu Thr Lys Met Gly Leu Arg Gly Phe Lys Asp Phe Tyr Ser Asp
        595                 600                 605

| | | | | | | | | | | | |
|---|---|---|---|---|---|---|---|---|---|---|---|
|Ser|Asn|Asp|Phe|Asp|Thr|Leu|Arg|Glu|Ala|Ala|Glu Glu Tyr Ala Asp|
| |610| | | |615| | | |620| | |

Gly Gly Ile Pro Val Thr Thr Thr Arg Pro Val Thr Tyr Gly Asp Ile
625                 630                 635                 640

Leu His Lys Gly Gly Lys Leu Ser Glu Ile Gly Arg Phe Arg Glu Ser
                645                 650                 655

Glu Arg Thr Leu Ser Ala Asp Met Asp Thr Lys Arg Arg Trp Asn Arg
            660                 665                 670

Thr Gly Ala Ser Phe Gly Arg Leu Leu Glu Gly Pro Glu Gly Ser Ala
        675                 680                 685

Pro Lys Val Tyr Asp Gly Glu Ala Leu Glu
    690                 695

<210> SEQ ID NO 9
<211> LENGTH: 2154
<212> TYPE: DNA
<213> ORGANISM: Salterprovirus His1

<400> SEQUENCE: 9

| | |
|---|---|
|atggcaaaat gcgataagtc gttagaagca atagatttgg atagggccta tactgcccca|60|
|agaaaagcaa agtgggcaga aaacaagaga atcaacggtt tagatacaga aacttcagac|120|
|ggtgatattt tctgtatttc agtctgttgg gaaggcgaaa aacctatggt gcaacacaac|180|
|gacagagaaa aacttacgtc taaacaagtc tggcaggttt aacagaccaa taaggcaaga|240|
|agttcgttaa atatgtggta taatcttgat tttgatgcta atgtagttct aaatcatgtt|300|
|tgctcggaag aacaattagc tgaattagtt gtttctggaa caacgttagc taatagcgat|360|
|agaacttaca ggcagtatat ggatacagat aaagagctac ggaaaggcga atatcttatt|420|
|acctacatac agtctaagtt cttagagatt aaagaccata actcacatat ctatacgcat|480|
|tatgatgctt cccaattctt ctacacgtca ttagaaaatg ctgttactga atggcttgga|540|
|gaatcgaagg cgaacgacgg gcttgaagcc gggcttttg ggtcacaaac acccaatcag|600|
|ctacgtgaaa ctgtagcaga atctgactgt gtaacatgga caaatcttag tctgacatac|660|
|aatgtctcta aaggcgataa atggacaata cataacgcca agagttatat tagtaaaaat|720|
|tggtcagata ttctcaaata tgcacaaatt gatgctgaat tagtacggga tttgtggcaa|780|
|gaagccgtaa acgtaggcga agaacttgat ataccaatgg gtaggcccctt tcaacgggc|840|
|taccttgctg aatcgtactt agataacagg cttcgggaga acccggctt agggcctatg|900|
|ccaatggcta aaatggcttg ggaaagctat gcaggtggta ggtttgaagt tctgaaacgg|960|
|ggaaatgtcg ggagagtagc agggccagat attaattctg cctaccctgc tgtattggca|1020|
|gaattaccag accctaaaac tctacggtgg aaaagagcaa acacgcaag tatttccgaa|1080|
|atagaaacgg cagactatgg atttatgaca gtaaaagttt cgacagaccc aacaagagaa|1140|
|atacagccat ttgcggtaaa agatgaaaaa caagataaat tggtatatcc ttccccacag|1200|
|aacacagaaa ttaccgttgt aaaagacata ttcatacacg catacaatca gggatatgtt|1260|
|acagattatg aagtaataga ctgttggtta ggctataaaa cagaaggtac tacttttccc|1320|
|tttgatttca taccagaatt atacgacaat aggaaaacag cagaagccaa cggattagag|1380|
|aaacgtggtt tactcttgaa aattgttctc aattcaatgt atgggaaaac ttgccaaacc|1440|
|acgccaaagc gtagagagtt agcagaatca acagaattag aattgcatga atcatatgta|1500|
|ccagatatgt ccctgccgaa aatgataaga gaaaagtatt cagaagggtt tatcgaatct|1560|
|cttactgccg gtgcatggtt taatccgttt ttggcttcat atattacagg attaacccgg|1620|

-continued

```
cttgagctac acaaacaaat ctgtaaacac gatttagaag aaaatactgt aatgctggct   1680
actgattgtg taatgattga agaaaagcca tttgaagaat cgaattttgt agagaactta   1740
gttcaagacg gcttaggata ttgggatatg aatataaag gcgatgcttt cgtacttggc   1800
gcgggagtgt accaaattga tttcgatact tgccagaaag gatgtaagga caattgtaac   1860
aagttctcac acaagcataa agtcaaaaca cgcggcttta gtgaagccga cttagaaaaa   1920
ggtcttgtta atgcggcaga aaaagccaac ggacatatag agatagaatc tacacgtcca   1980
cagactattt cagaaatcat ttggtctaat gaagaattat cgcaagttgg aaactttta    2040 gaacaggaaa gaaaaatcaa accggaaatg gatactaaga ggaaatggtc tgaaaacaca   2100
gactttaaga aactgttaag tacgtgcgaa acatccttac cattgaagat atga         2154
```

<210> SEQ ID NO 10
<211> LENGTH: 717
<212> TYPE: PRT
<213> ORGANISM: Salterprovirus His1

<400> SEQUENCE: 10

```
Met Ala Lys Cys Asp Lys Ser Leu Glu Ala Ile Asp Leu Asp Arg Ala
1               5                   10                  15

Tyr Thr Ala Pro Arg Lys Ala Lys Trp Ala Glu Asn Lys Arg Ile Asn
            20                  25                  30

Gly Leu Asp Thr Glu Thr Ser Asp Gly Asp Ile Phe Cys Ile Ser Val
        35                  40                  45

Cys Trp Glu Gly Glu Lys Pro Met Val Gln His Asn Asp Arg Glu Lys
    50                  55                  60

Leu Thr Ser Lys Gln Val Trp Gln Val Leu Thr Asp His Lys Ala Arg
65                  70                  75                  80

Ser Ser Leu Asn Met Trp Tyr Asn Leu Asp Phe Asp Ala Asn Val Val
                85                  90                  95

Leu Asn His Val Cys Ser Glu Glu Gln Leu Ala Glu Leu Val Val Ser
            100                 105                 110

Gly Thr Thr Leu Ala Asn Ser Asp Arg Thr Tyr Arg Gln Tyr Met Asp
        115                 120                 125

Thr Asp Lys Glu Leu Arg Lys Gly Glu Tyr Leu Ile Thr Tyr Ile Gln
    130                 135                 140

Ser Lys Phe Leu Glu Ile Lys Asp His Asn Ser His Ile Tyr Thr His
145                 150                 155                 160

Tyr Asp Ala Ser Gln Phe Phe Tyr Thr Ser Leu Glu Asn Ala Val Thr
                165                 170                 175

Glu Trp Leu Gly Glu Ser Lys Ala Asn Asp Gly Leu Glu Ala Gly Leu
            180                 185                 190

Phe Gly Ser Gln Thr Pro Asn Gln Leu Arg Glu Thr Val Ala Glu Ser
        195                 200                 205

Asp Cys Val Thr Trp Thr Asn Leu Ser Leu Thr Tyr Asn Val Ser Lys
    210                 215                 220

Gly Asp Lys Trp Thr Ile His Asn Ala Lys Ser Tyr Ile Ser Lys Asn
225                 230                 235                 240

Trp Ser Asp Ile Leu Lys Tyr Ala Gln Ile Ala Glu Leu Val Arg
                245                 250                 255

Asp Leu Trp Gln Glu Ala Val Asn Val Gly Glu Glu Leu Asp Ile Pro
            260                 265                 270

Met Gly Arg Pro Phe Ser Thr Gly Tyr Leu Ala Glu Ser Tyr Leu Asp
```

```
            275                 280                 285
Asn Arg Leu Arg Glu Lys Pro Gly Leu Gly Pro Met Pro Met Ala Lys
290                 295                 300
Met Ala Trp Glu Ser Tyr Ala Gly Gly Arg Phe Glu Val Leu Lys Arg
305                 310                 315                 320
Gly Asn Val Gly Arg Val Ala Gly Pro Asp Ile Asn Ser Ala Tyr Pro
                325                 330                 335
Ala Val Leu Ala Glu Leu Pro Asp Pro Lys Thr Leu Arg Trp Lys Arg
            340                 345                 350
Ala Lys His Ala Ser Ile Ser Glu Ile Glu Thr Ala Asp Tyr Gly Phe
        355                 360                 365
Met Thr Val Lys Val Ser Thr Asp Pro Thr Arg Glu Ile Gln Pro Phe
    370                 375                 380
Ala Val Lys Asp Glu Lys Gln Asp Lys Leu Val Tyr Pro Ser Pro Gln
385                 390                 395                 400
Asn Thr Glu Ile Thr Val Val Lys Asp Ile Phe Ile His Ala Tyr Asn
                405                 410                 415
Gln Gly Tyr Val Thr Asp Tyr Glu Val Ile Asp Cys Trp Leu Gly Tyr
            420                 425                 430
Lys Thr Glu Gly Thr Thr Phe Pro Phe Asp Phe Ile Pro Glu Leu Tyr
        435                 440                 445
Asp Asn Arg Lys Thr Ala Glu Ala Asn Gly Leu Glu Lys Arg Gly Leu
    450                 455                 460
Leu Leu Lys Ile Val Leu Asn Ser Met Tyr Gly Lys Thr Cys Gln Thr
465                 470                 475                 480
Thr Pro Lys Arg Arg Glu Leu Ala Glu Ser Thr Glu Leu Glu Leu His
                485                 490                 495
Glu Ser Tyr Val Pro Asp Met Ser Leu Pro Lys Met Ile Arg Glu Lys
            500                 505                 510
Tyr Ser Glu Gly Phe Ile Glu Ser Leu Thr Ala Gly Ala Trp Phe Asn
        515                 520                 525
Pro Phe Leu Ala Ser Tyr Ile Thr Gly Leu Thr Arg Leu Glu Leu His
    530                 535                 540
Lys Gln Ile Cys Lys His Asp Leu Glu Glu Asn Thr Val Met Leu Ala
545                 550                 555                 560
Thr Asp Cys Val Met Ile Glu Glu Lys Pro Phe Glu Glu Ser Asn Phe
                565                 570                 575
Val Glu Asn Leu Val Gln Asp Gly Leu Gly Tyr Trp Asp Met Glu Tyr
            580                 585                 590
Lys Gly Asp Ala Phe Val Leu Gly Ala Gly Val Tyr Gln Ile Asp Phe
        595                 600                 605
Asp Thr Cys Gln Lys Gly Cys Lys Asp Asn Cys Asn Lys Phe Ser His
    610                 615                 620
Lys His Lys Val Lys Thr Arg Gly Phe Ser Glu Ala Asp Leu Glu Lys
625                 630                 635                 640
Gly Leu Val Asn Ala Ala Glu Lys Ala Asn Gly His Ile Glu Ile Glu
                645                 650                 655
Ser Thr Arg Pro Gln Thr Ile Ser Glu Ile Trp Ser Asn Glu Glu
            660                 665                 670
Leu Ser Gln Val Gly Asn Phe Leu Glu Gln Glu Arg Lys Ile Lys Pro
        675                 680                 685
Glu Met Asp Thr Lys Arg Lys Trp Ser Glu Asn Thr Asp Phe Lys Lys
    690                 695                 700
```

Leu Leu Ser Thr Cys Glu Thr Ser Leu Pro Leu Lys Ile
705                 710                 715

<210> SEQ ID NO 11
<211> LENGTH: 2163
<212> TYPE: DNA
<213> ORGANISM: Salterprovirus His2

<400> SEQUENCE: 11

| | | | | | |
|---|---|---|---|---|---|
| atggcaaaat | ctgatagaaa | cttagatgaa | gttaacttat | atcctgcata | tcaagaccaa | 60 |
| tatagcgcaa | cgtttgtaga | tggtaaactg | attaatgcat | ttgatacgga | aacatcaagc | 120 |
| ggtactgtat | ttatgcttac | atccgcgtat | ggcgataaga | cacaagcata | ctacaacaga | 180 |
| gatgtttccg | aattagatgc | agaaactatc | atggatgcat | tgacggatta | caagacaaga | 240 |
| agtaacatca | atatatggta | caatcttgat | ttcgatgcaa | acgccattct | atccggcata | 300 |
| ctgtcacaaa | aagaaatgtc | ggaattagtc | gtaacgaatg | aaacaactac | aaccgttgca | 360 |
| ggtatcgaat | acgaaatatt | ttacatcaaa | ggtaagatgt | tacgcattgt | tgatgaaaat | 420 |
| ggtaatatct | caccgcatta | cgatattgcc | caattcttct | atacttcatt | agataacgcg | 480 |
| gccgaagaat | ggttaggtga | aaacaagaaa | gaaggtattg | atacatccaa | gttcgatgat | 540 |
| aaagaataca | tcaaagataa | ctttgatgaa | atcttgaaat | acgcaaagaa | agatgcaagt | 600 |
| cttacgcaag | accttgccat | tgaactaacg | aatgaagcgg | aaaatttaga | tattcctatg | 660 |
| ggtaggccaa | taagtacggg | atatcttagt | gcggaatacc | tacgtgcaaa | taccgaagaa | 720 |
| aagccttccc | ttggtaatga | ggcaatgcaa | aatctgtttt | gggaaagtta | ctatggcgga | 780 |
| aggtttgaag | tgttccaaag | gggtaatgtc | ggtgaagttg | ttgcaccgga | tatcaattca | 840 |
| gcatatccgg | caatcatgaa | ggacttaccg | gacccaacta | cgcttaattg | gaatcactac | 900 |
| ttgaatgaag | taagcgataa | agagcctttc | tcacattcta | tcaataagtt | cggttatgag | 960 |
| gaaatagaaa | atgggcatta | cggtgttgtg | aaagcaagag | taacgacaga | ttccagtaga | 1020 |
| atgatacaac | cgtttgcgtg | taagattgac | gggaaagtga | aattcccggc | aatgacaaat | 1080 |
| aaggttgtta | ccgttatcaa | gcccattttc | gaattcgccg | taaacaacgg | attagttacg | 1140 |
| gatttcgaat | taattgaagc | gtggatagga | acattacag | ataggacaag | taagcccttc | 1200 |
| gaatttatag | gggatatgta | tgcagaacgt | aaagtattcg | aacagctaaa | gaacaaaccg | 1260 |
| aagaaagggc | aattgctgaa | aattgttctc | aattcatcgt | atggcaaaac | gtgccagaca | 1320 |
| acagaaaaga | gacataagca | tgacttagac | aaagacggca | aaaagataat | gcaagcacat | 1380 |
| gaaacgcaat | accgcgtttt | ctatctctcc | aaaaagcaac | gtgaagccct | tggagatgat | 1440 |
| gaaatcatca | ttacggaatt | agaagcgggc | aagcgattca | atccgttctt | tgcgtcttac | 1500 |
| attaccggat | tgacgcgctt | agaactacat | aagcaagttg | ttgaacatga | cattgaagat | 1560 |
| agtacggtaa | tgttcgcaac | ggattgccta | atggtggaaa | aagaggcata | tgaaaattcc | 1620 |
| tcattcgatg | aacagataca | cgtaccggat | gattcactac | agaaagtgaa | attccgaaaa | 1680 |
| gaagctacac | gttcattggg | tgcatgggat | ttcgattatg | aaggtagtgc | gtttattgtc | 1740 |
| ggtagtggcg | tgtatgaggt | agataccatt | caaggtaaga | ccaaaacgaa | aacgcgcgga | 1800 |
| ttcattgaat | cgaacttagg | cgatacgttg | aaaggacttg | caagaaaca | caagagggca | 1860 |
| ataccattag | ataatgaacg | gccgttaaca | atggcggaag | tgttgataaa | tacagaacgt | 1920 |
| ggtagtgtgt | cggaattcgt | ggaaaactcc | aagaaactaa | aacccgactt | tgacgacaag | 1980 |
| cgtaactgga | atcgggaaaa | tccaaatttc | cacgacttgc | taaacgacaa | agagtatagt | 2040 |

```
aaaccgatag acttgcaaga gcaaaaagaa gaaatgatac aagaacaaat ggatatcaat    2100
gaaaagatga taggcgatgc aacaccgaac ggaaacgaaa cggttgtggt aaaagatgat    2160
taa                                                                  2163
```

<210> SEQ ID NO 12
<211> LENGTH: 720
<212> TYPE: PRT
<213> ORGANISM: Salterprovirus His2

<400> SEQUENCE: 12

```
Met Ala Lys Ser Asp Arg Asn Leu Asp Glu Val Asn Leu Tyr Pro Ala
1               5                   10                  15

Tyr Gln Asp Gln Tyr Ser Ala Thr Phe Val Asp Gly Lys Leu Ile Asn
            20                  25                  30

Ala Phe Asp Thr Glu Thr Ser Ser Gly Thr Val Phe Met Leu Thr Ser
        35                  40                  45

Ala Tyr Gly Asp Lys Thr Gln Ala Tyr Tyr Asn Arg Asp Val Ser Glu
    50                  55                  60

Leu Asp Ala Glu Thr Ile Met Asp Ala Leu Thr Asp Tyr Lys Thr Arg
65                  70                  75                  80

Ser Asn Ile Asn Ile Trp Tyr Asn Leu Asp Phe Asp Ala Asn Ala Ile
                85                  90                  95

Leu Ser Gly Ile Leu Ser Gln Lys Glu Met Ser Glu Leu Val Val Thr
            100                 105                 110

Asn Glu Thr Thr Thr Thr Val Ala Gly Ile Glu Tyr Glu Ile Phe Tyr
        115                 120                 125

Ile Lys Gly Lys Met Leu Arg Ile Val Asp Glu Asn Gly Asn Ile Ser
    130                 135                 140

Pro His Tyr Asp Ile Ala Gln Phe Phe Tyr Thr Ser Leu Asp Asn Ala
145                 150                 155                 160

Ala Glu Glu Trp Leu Gly Glu Asn Lys Lys Gly Ile Asp Thr Ser
                165                 170                 175

Lys Phe Asp Asp Lys Glu Tyr Ile Lys Asp Asn Phe Asp Glu Ile Leu
            180                 185                 190

Lys Tyr Ala Lys Lys Asp Ala Ser Leu Thr Gln Asp Leu Ala Ile Glu
        195                 200                 205

Leu Thr Asn Glu Ala Glu Asn Leu Asp Ile Pro Met Gly Arg Pro Ile
    210                 215                 220

Ser Thr Gly Tyr Leu Ser Ala Glu Tyr Leu Arg Ala Asn Thr Glu Glu
225                 230                 235                 240

Lys Pro Ser Leu Gly Asn Glu Ala Met Gln Asn Leu Phe Trp Glu Ser
                245                 250                 255

Tyr Tyr Gly Gly Arg Phe Glu Val Phe Gln Arg Gly Asn Val Gly Glu
            260                 265                 270

Val Val Ala Pro Asp Ile Asn Ser Ala Tyr Pro Ala Ile Met Lys Asp
        275                 280                 285

Leu Pro Asp Pro Thr Thr Leu Asn Trp Asn His Tyr Leu Asn Glu Val
    290                 295                 300

Ser Asp Lys Glu Pro Phe Ser His Ser Ile Asn Lys Phe Gly Tyr Glu
305                 310                 315                 320

Glu Ile Glu Asn Gly His Tyr Gly Val Val Lys Ala Arg Val Thr Thr
                325                 330                 335

Asp Ser Ser Arg Met Ile Gln Pro Phe Ala Cys Lys Ile Asp Gly Lys
```

```
              340                 345                 350
Val Lys Phe Pro Ala Met Thr Asn Lys Val Thr Val Ile Lys Pro
            355                 360                 365
Ile Phe Glu Phe Ala Val Asn Asn Gly Leu Val Thr Asp Phe Glu Leu
        370                 375                 380
Ile Glu Ala Trp Ile Gly Asn Ile Thr Asp Arg Thr Ser Lys Pro Phe
385                 390                 395                 400
Glu Phe Ile Gly Asp Met Tyr Ala Glu Arg Lys Val Phe Glu Gln Leu
                405                 410                 415
Lys Asn Lys Pro Lys Lys Gly Gln Leu Leu Lys Ile Val Leu Asn Ser
            420                 425                 430
Ser Tyr Gly Lys Thr Cys Gln Thr Thr Glu Lys Arg His Lys His Asp
        435                 440                 445
Leu Asp Lys Asp Gly Lys Lys Ile Met Gln Ala His Glu Thr Gln Tyr
        450                 455                 460
Pro Arg Phe Tyr Leu Ser Lys Lys Gln Arg Glu Ala Leu Gly Asp Asp
465                 470                 475                 480
Glu Ile Ile Ile Thr Glu Leu Glu Ala Gly Lys Arg Phe Asn Pro Phe
                485                 490                 495
Phe Ala Ser Tyr Ile Thr Gly Leu Thr Arg Leu Glu Leu His Lys Gln
                500                 505                 510
Val Val Glu His Asp Ile Glu Asp Ser Thr Val Met Phe Ala Thr Asp
            515                 520                 525
Cys Leu Met Val Glu Lys Glu Ala Tyr Glu Asn Ser Ser Phe Asp Glu
        530                 535                 540
Gln Ile His Val Pro Asp Asp Ser Leu Pro Glu Ser Glu Phe Arg Lys
545                 550                 555                 560
Glu Ala Thr Arg Ser Leu Gly Ala Trp Asp Phe Asp Tyr Glu Gly Ser
                565                 570                 575
Ala Phe Ile Val Gly Ser Gly Val Tyr Glu Val Asp Thr Ile Gln Gly
            580                 585                 590
Lys Thr Lys Thr Lys Thr Arg Gly Phe Ile Glu Ser Asn Leu Gly Asp
        595                 600                 605
Thr Leu Lys Gly Leu Ala Lys Lys His Lys Glu Ala Ile Pro Leu Asp
        610                 615                 620
Asn Glu Arg Pro Leu Thr Met Ala Glu Val Leu Ile Asn Thr Glu Arg
625                 630                 635                 640
Gly Ser Val Ser Glu Phe Val Glu Asn Ser Lys Lys Leu Lys Pro Asp
                645                 650                 655
Phe Asp Asp Lys Arg Asn Trp Asn Arg Glu Asn Pro Asn Phe His Asp
                660                 665                 670
Leu Leu Asn Asp Lys Glu Tyr Ser Lys Pro Ile Asp Leu Gln Glu Gln
            675                 680                 685
Lys Glu Glu Met Ile Gln Glu Gln Met Asp Ile Asn Glu Lys Met Ile
        690                 695                 700
Gly Asp Ala Thr Pro Asn Gly Asn Glu Thr Val Val Lys Asp Asp
705                 710                 715                 720

<210> SEQ ID NO 13
<211> LENGTH: 575
<212> TYPE: PRT
<213> ORGANISM: Bacillus virus phi29

<400> SEQUENCE: 13
```

```
Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asn Leu Lys
50                  55                  60

Phe Asp Gly Ala Phe Ile Ile Asn Trp Leu Glu Arg Asn Gly Phe Lys
65              70                  75                  80

Trp Ser Ala Asp Gly Leu Pro Asn Thr Tyr Asn Thr Ile Ile Ser Arg
            85                  90                  95

Met Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
            115                 120                 125

Pro Val Lys Lys Ile Ala Lys Asp Phe Lys Leu Thr Val Leu Lys Gly
        130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ala Glu Ala
            165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Phe Lys
        195                 200                 205

Lys Val Phe Pro Thr Leu Ser Leu Gly Leu Asp Lys Glu Val Arg Tyr
        210                 215                 220

Ala Tyr Arg Gly Gly Phe Thr Trp Leu Asn Asp Arg Phe Lys Glu Lys
225                 230                 235                 240

Glu Ile Gly Glu Gly Met Val Phe Asp Val Asn Ser Leu Tyr Pro Ala
            245                 250                 255

Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
        275                 280                 285

Arg Cys Glu Phe Glu Leu Lys Glu Gly Tyr Ile Pro Thr Ile Gln Ile
        290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
            325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Thr
        355                 360                 365

Tyr Ile Lys Thr Thr Ser Glu Gly Ala Ile Lys Gln Leu Ala Lys Leu
        370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
            405                 410                 415

Gly Glu Glu Glu Thr Lys Asp Pro Val Tyr Thr Pro Met Gly Val Phe
```

|     |     |     |     |     | 420 |     |     |     |     | 425 |     |     |     |     | 430 |     |     |     |     |
|-----|-----|-----|-----|-----|-----|-----|-----|-----|-----|-----|-----|-----|-----|-----|-----|-----|-----|-----|-----|
| Ile | Thr | Ala | Trp | Ala | Arg | Tyr | Thr | Thr | Ile | Thr | Ala | Ala | Gln | Ala | Cys |
|     |     |     | 435 |     |     |     |     | 440 |     |     |     |     | 445 |     |     |
| Tyr | Asp | Arg | Ile | Ile | Tyr | Cys | Asp | Thr | Asp | Ser | Ile | His | Leu | Thr | Gly |
|     |     | 450 |     |     |     |     | 455 |     |     |     | 460 |     |     |     |     |
| Thr | Glu | Ile | Pro | Asp | Val | Ile | Lys | Asp | Ile | Val | Asp | Pro | Lys | Lys | Leu |
| 465 |     |     |     |     | 470 |     |     |     |     | 475 |     |     |     |     | 480 |
| Gly | Tyr | Trp | Ala | His | Glu | Ser | Thr | Phe | Lys | Arg | Ala | Lys | Tyr | Leu | Arg |
|     |     |     |     | 485 |     |     |     |     | 490 |     |     |     |     | 495 |     |
| Gln | Lys | Thr | Tyr | Ile | Gln | Asp | Ile | Tyr | Met | Lys | Glu | Val | Asp | Gly | Lys |
|     |     |     | 500 |     |     |     |     | 505 |     |     |     |     | 510 |     |     |
| Leu | Val | Glu | Gly | Ser | Pro | Asp | Asp | Tyr | Thr | Asp | Ile | Lys | Phe | Ser | Val |
|     |     | 515 |     |     |     |     | 520 |     |     |     |     | 525 |     |     |     |
| Lys | Cys | Ala | Gly | Met | Thr | Asp | Lys | Ile | Lys | Lys | Glu | Val | Thr | Phe | Glu |
|     | 530 |     |     |     |     | 535 |     |     |     |     | 540 |     |     |     |     |
| Asn | Phe | Lys | Val | Gly | Phe | Ser | Arg | Lys | Met | Lys | Pro | Lys | Pro | Val | Gln |
| 545 |     |     |     |     | 550 |     |     |     |     | 555 |     |     |     |     | 560 |
| Val | Pro | Gly | Gly | Val | Val | Leu | Val | Asp | Asp | Thr | Phe | Thr | Ile | Lys |     |
|     |     |     |     | 565 |     |     |     |     | 570 |     |     |     |     | 575 |     |